(12) United States Patent
Waddell

(10) Patent No.: US 10,951,985 B1
(45) Date of Patent: Mar. 16, 2021

(54) METHOD AND SYSTEM FOR AUDIO CRITICAL LISTENING AND EVALUATION

(71) Applicant: Gebre Waddell, Memphis, TN (US)

(72) Inventor: Gebre Waddell, Memphis, TN (US)

( * ) Notice: Subject to any disclaimer, the term of this patent is extended or adjusted under 35 U.S.C. 154(b) by 0 days.

(21) Appl. No.: 15/641,212

(22) Filed: Jul. 4, 2017

Related U.S. Application Data

(60) Provisional application No. 62/357,931, filed on Jul. 1, 2016.

(51) Int. Cl.

| | |
|---|---|
| *H04R 3/04* | (2006.01) |
| *G10L 21/0232* | (2013.01) |
| *G10L 21/038* | (2013.01) |
| *A61B 5/00* | (2006.01) |
| *G08B 21/24* | (2006.01) |
| *A61B 5/12* | (2006.01) |
| *H04H 60/04* | (2008.01) |

(52) U.S. Cl.
CPC ............... *H04R 3/04* (2013.01); *A61B 5/12* (2013.01); *A61B 5/746* (2013.01); *G08B 21/24* (2013.01); *G10L 21/0232* (2013.01); *G10L 21/038* (2013.01); *H04H 60/04* (2013.01)

(58) Field of Classification Search
CPC ............ H04R 3/04; H04R 3/14; H04H 60/04
USPC ............................ 381/119, 103, 94.2, 98, 61
See application file for complete search history.

(56) References Cited

U.S. PATENT DOCUMENTS

| | | | | |
|---|---|---|---|---|
| 8,917,876 | B2 * | 12/2014 | Goldstein | G01H 3/14 381/56 |
| 9,794,688 | B2 * | 10/2017 | You | H04R 3/04 |
| 10,433,089 | B2 * | 10/2019 | Wilson | H03G 3/32 |
| 2001/0036278 | A1 * | 11/2001 | Polisset | H04R 3/04 381/61 |
| 2006/0098827 | A1 * | 5/2006 | Paddock | G10L 21/02 381/106 |
| 2012/0008788 | A1 * | 1/2012 | Jonsson | H04R 3/04 381/17 |
| 2014/0037111 | A1 * | 2/2014 | Uhle | H04H 60/04 381/119 |
| 2017/0215020 | A1 * | 7/2017 | Robinson | H04R 5/02 |

* cited by examiner

*Primary Examiner* — Disler Paul
(74) *Attorney, Agent, or Firm* — William S. Parks

(57) ABSTRACT

Disclosed herein is a method of constructing and utilizing a sound engineering evaluation and comparison process to allow for improved finished results. Such a method entails the utilization of a high-pass filter for listening evaluation of recorded music or sounds including consistency with low-frequency mixing to allow for a tool to implement changes in relation to the filtered results in order to accommodate sensitivities of the human ear (with the optional inclusion of a comparison method to provide possible further enhanced results and the avoidance of biases). In such a manner, a facilitating method for sound engineering mixing adjustments that provide such accommodations are provided for improved sound recordings for distribution within on-line or recording product frameworks.

1 Claim, 10 Drawing Sheets

FIGURE 1. Auratone Frequency Response

FIGURE 2. NS10 Frequency Response

Equal-loudness contours from ISO 226:2003 revision
Original ISO standard shown for 40-phons

FIGURE 3. ISO 226:2003 Equal Loudness Contours

METHOD AND SYSTEM FOR AUDIO CRITICAL LISTENING AND EVALUATION

CROSS-REFERENCE TO RELATED APPLICATION

This application claims benefit of U.S. Provisional Patent Application No. 62/357,931, filed Jul. 1, 2016, the entirety of such prior application incorporated herein by reference.

FIELD OF THE INVENTION

Disclosed herein is a method of constructing and utilizing a sound engineering evaluation and comparison process to allow for improved finished results. Such a method entails the utilization of a high-pass filter for listening evaluation of recorded music or sounds including consistency with low-frequency mixing to allow for a tool to implement changes in relation to the filtered results in order to accommodate sensitivities of the human ear (with the optional inclusion of a comparison method to provide possible further enhanced results and the avoidance of biases). In such a manner, a facilitating method for sound engineering mixing adjustments that provide such accommodations are provided for improved sound recordings for distribution within on-line or recording product frameworks.

BACKGROUND OF THE PRIOR ART

Sound engineers must provide high quality to achieve success. Quality largely relates to how decisions are made and how recordings are evaluated. In the earliest days of recording, sound engineers were working to find ways to improve recordings by taking care in their evaluation processes and the factors that affected them. Acoustic architecture, carefully crafted listening systems, and even the hearing ability of the engineer all were and have continued to be factors of consideration.

Classic recording techniques may have been effective because of reasons that were not accurately recognized at their inception. After recognition, the reasons could be made more effective, and formed into powerful, simple tools for sound engineers. For instance, there has occurred research in the area of sound engineering about the sensitivity of the human ear, evaluation of recorded audio, and about details of tools that could be deployed in evaluation. However, there is not a body of research that describes the totality of recent understandings together with classic techniques. Also, the underlying reason that the classic techniques have been so effective they may have been, again, misunderstood.

In the past, for instance, there have been systems that allow for adjustments of the loudness of a signal in real time. However, in such a situation, such an adjustment is not based on another signal and it is not used for comparison to improve the recorded sound in relation to human hearing issues. This type of system is thus limited to adjusting loudness depending on a flow of audio through the system itself, rather than adjusting it to match another source subsequent to recording. Additionally, such a system does not contain the audio comparison methods including blind and randomized testing.

Another type of system includes the adjustment of loudness of at least one channel of audio, depending on another, with filtering to approximate the human hearing system. This is accomplished by comparing phase and samples of phase, and primarily for voice or background noise. This does not cover specifics in terms of comparisons between frequencies, nor does it contain audio comparison methods including blind and randomized testing.

Another type of system provides consistent loudness across one or more input tracks, however it uses a modified limiter, where the loudness adjustment portion of the comparison method only uses a gain control. This system thus does not actually minimize any potential artifacts in the signal that might be introduced by limiting, maintaining signal purity for high quality evaluations, rather than direct comparisons, nor does it contain the audio comparison methods including blind and randomized testing.

Yet another system involves monitoring of sound pressure levels at the ear using an ear canal microphone, ostensibly to preserve ear health. It calculates data to detect such potential damage levels. This system does not measure signal coming through it to measure simple ear fatigue in order to help sound engineers avoid making misjudgments in sound levels during mixing.

Additionally, there are systems that monitor SPL levels with a transducer placed in the ear. This system, however, does not do anything to detect audio flowing through it for the purpose of combining with timers to provide visual feedback about when ear fatigue may be a factor in sound engineering decisions.

Geoff Emerick was an audio engineer who worked with The Beatles, on albums including Sgt. Pepper's Lonely Hearts Club Band, Revolver, Magical Mystery Tour and Abbey Road. Emerick has described techniques of sounds mixing wherein all tracks would be mixed without the bass guitar track, allowing for such a bass track to be brought up and mixed only as the final step. He would start by bringing the mix without the bass guitar to −2 on the VU meter. Later, when the bass would be mixed in, the VU meter would be pushed up to 0. Emerick explains that in this way, at the final step, the bass was 2 dB VU above everything else. The Beatles are generally known for having recordings that had a prominent sound for their time and this technique may have been central to the difference in recording quality.

Bruce Swedien is one of the most noted engineers in the recording industry. He worked with Michael Jackson on many albums including Thriller, the best-selling album of all time. Mr. Swedien has stated that his work always checked everything on speakers called Auratones, devices he has repeatedly referred to as "truth speakers". Mr. Swedien has further repeatedly noted that he has never liked headphones, or car stereos, and he has always felt it is foolish to check professional mixes on such implements. To him and his level of expertise, the ability to achieve a good sound mix on Auratones is an indication such will sound great anywhere. Thus, to him, the mark of a good recording is to sound good anywhere, without requiring high-volume playback over high-end speakers. Auratones do not produce much bass, as shown in its frequency response in Prior Art FIG. 1.

Yamaha NS10 speakers are a studio classic and perhaps the most widely-recognized studio speaker of all time. The NS10 speakers, when designed and launched in 1978 were technically unremarkable, having been designed for consumer listening at home. These speakers did not become popular for such home listening purposes and the product all but disappeared from the marketplace. However, artist turned engineers started using them, and perhaps most influential of all, famed engineer Bob Clearmountain began publicizing his use of them. Clearmountain wanted a speaker he could take from studio-to-studio and he chose the NS10 because it was "the worst-sounding speaker" he could find. Virtually all professional engineers have heard of Clearmountain's use of tissue paper over the NS10 tweeters to dull their brightness. Yamaha NS10s do not produce much bass, as shown in its frequency response in Prior Art FIG. 2.

Next, we consider the frequency response of the human ear. The frequency sensitivity of the ear is such that we are most sensitive around 3 kHz, and we are least sensitive to bass, as well as the highest frequencies as we approach the human hearing limit at 20 kHz. The frequency sensitivity of the ear was first outlined as the Fletcher-Munson curves in 1933, re-determined and published as Robinson-Dadson curves in 1956, and most recently revised by the International Standards Organization in (ISO 226:2003). The human ear is not very sensitive to bass, as shown in its frequency sensitivity in Prior Art FIG. 3, recreated from (ISO 226:2003).

Noted audio engineer Paul Frindle, has worked over 40 years as a designer at the famed SSL Corporation, on the Sony Oxford processors and is the sole creator of the Dynamic Spectrum Mapper. Past descriptions exists regarding the effect of high pass filtering on a generated tone of approximately 100 Hz. He shows that it changes significantly when high pass filtering is applied, even though it is of a range that would not show to be affected by the filter in an FFT representation of the filter's frequency response curve. He discusses that because NS10s have a roll-off that they are essentially functioning as a high-pass filter and thus would impart similar characteristics shown using the digital pass filter in his illustration. Importantly, however, these high pass filter actions are undertaken while recording; applications to fully recorded tracks have never been mentioned or performed.

To filter out bass frequencies, a high pass filter is used. There are several types of high pass filters and many ways they can function and be constructed. Different filter types are compared to each other. This source covers them for their use in crossover design. The finding is that Bessel type has the widest, most gradual crossover region and a gentle dip in the summed response. The Linkwitz-Riley type has a moderate roll-off and a flat sum. The Butterworth type has the sharpest initial cutoff and a +3 dB sum at the crossover.

Filters have a type and also have an order, which in digital filter architecture involves the number of samples a filter "looks back" and mixes with the new input. The benefits of high-order parametric filtering are present in certain past systems, as well. Higher order filtering can give more accuracy, especially around the passband with the potential for $4^{th}$ or at most $6^{th}$ order filtering to gain accuracy.

It is well-known and widely quoted research that explains that we can detect differences in loudness of approximately 0.41 dB SPL at a threshold of over 30 dB SPL and above.

There is a device described in the past regarding an audio comparison device which includes a voting element and the details of a hardware device to accomplish the comparison. It does not appear that the claims cover devices that would not include voting elements. No loudness matching algorithm is included in this device.

Loudness matching devices have been described, as well, with a limiter having a target threshold with signals below the target threshold are adjusted upwardly and a second copy is output based on the analysis.

Issues with ABX testing are discussed in other situations, particularly showing that there are more sophisticated analysis schemes such as signal detection theory that could prevent false conclusions and account for certain biases. There is a caveat that the foundation of any good experiment is the experimental design and that the statistical analysis itself will not overcome issues with such design. Certain reporting should thus go with all listening tests, including the details of any apparatuses used should be included in all listening tests as well as the environment, test setup and listening material. It has been determined, now, that testing should be double blind and include a third x "random" element, aside a simple A/B test. These elements are great for conducting statistical research but may not be the very best for the recording studio user workflow.

The concept that visual stimuli affects human judgment of auditory loudness has been considered, as well, in the past. Testing was conducted on individuals in this regard and found that prediction error is a factor of "crossmodal interplay" between vision and audition. The conclusion is that what we see can affect what we hear.

Three categories may be used to classify sound during evaluation, particularly three main divisions for evaluation (1) stimulus-response (2) Pleasantness of sounds and (3) identifiability of sounds or sound sources. With the instant research we are concerned with the pleasantness of sounds, for which this research indicates is done by means of rating scales.

The evaluation of audio in terms of its spatial sound quality is has been considered in the past. Such concerns intend to supersede the International Telecommunication Union (ITU) recommended test methods, as they do not take into account the spatial dimension of sound. When working in professional sound engineering, the spatial aspect of a recording is of prime importance.

In any case, the important considerations in the past were the separate capabilities of such prior devices to seek either a means to achieve audio results for non-bass tracks that either maximize in relation to human ear sensitivity levels (as recorded) or the capability of providing linear low-distortion audio effects within the final recorded format. Thus, such prior art standards were one or the other with the utilization of a high pass filter (HPF) providing linear audio effects without unintended qualities (including a too-loud vocal, a too-soft snare, a problematic cymbal, as mere examples), possible low-distortion (due to a filter utilization, rather than a speaker system basis as in the prior art), linear results or standard mixing boards providing maximum ear sensitivity levels at the specific frequency but with large amounts of audio distortions (and/or unintended sound qualities as noted above). In either situation, the resultant recordings provided the consumer market would either have low distortions at the non-bass track level or high distortion levels at the non-bass track level, but with maximum ear sensitivity frequency levels, leaving much to be desired and no understood means to overcome the clear deficiencies in these respects.

As it pertains to bass levels in market-supplied recordings, there are also problems with the currently standard operations. Bass tracks are typically honed after recording has been undertaken through single audio filtering, ostensibly providing such action to the overall recorded track alone. In this situation, thus, such single bass track filtering results in noticeably limited effects, particularly with dominant bass lines in comparison with the remaining non-bass track results. In other words, such standard bass treatments singularly focus on single frequency effects, lacking complementary mixing results for reintroduction with the non-bass track lines components of a recording. Such a common situation creates a bass-dominating, rather than overall blended bass and non-bass recording mix, resulting in rather harsh audio finishing, particularly when combined with the aforementioned non-bass filtered components that are limited to maximized ear sensitivity levels or low distortions, not both. Improvements in such recording results within the marketed recorded music industry would be desired, certainly, but are lacking within the current state.

Additionally, it has been understood that sound engineers, particularly, are susceptible to ear fatigue when continuously subjected to recorded music, whether in terms of individual tracks or combined mixed tracks. If such a sound engineer suffers too much ear fatigue at a single sitting, such a person would lack a proper perspective to genuinely judge the levels of mixing adjustments needed to correctly provide finished recorded products for market. Thus, the ability to alert a subject sound engineer of music exposure time period durations in order to determine the needed rest time between effective mixing operations would be helpful for overall optimization of such considerations, as well. To date, some alerts are undertaken through setting external clocks. However, there is nothing provided integrated within an overall recorded music mixing program. Thus, overall there is nothing in the art providing any recorded music mixing capabilities of any of these three bases.

To the contrary, the present system provides totally divergent methods and processes from the state of the art present today. Here it was discovered how to construct an optimal high-pass filter for listening evaluation, a bass leveling two-frequency method, an ear fatigue reminder system, and, optionally, the construction of a comparison tool to overcome human ear fatigue in relation to recorded sounds and/or music.

Advantages and Summary of the Disclosure

A particular advantage of the present disclosure is the overall capability of the system to provide an effect that thoroughly mixes a non-bass track with a resultant maximum ear sensitivity level plus low distortion effects after recording with an audio adjusted two-level bass track for maximum effects on any type of listening platform, whether amplifier, headphone, and the like, particularly compared with past mixing configurations. Another advantage of the overall system is the ability of the sound engineer user to apply a high-pass filter to a recorded non-bass track to accomplish the above-noted maximum ear sensitivity/low distortion results, as compared with the typical application of a high-pass filter to recording sources (microphones) for individual linear distortion effect reductions alone. Another advantage of this inventive disclosure is the capability of the subject sound engineer to separate the bass track component(s) into two separate levels for upper and lower frequency comparative audio mixing treatments to optimize the bass effects prior to reintroduction with the non-bass track component(s), garnering a more balanced and thoroughly blended bass track component within an overall finished audio product. Thus, another advantage is the overall effect of optimized overall ear sensitivity blended musical recording results that sound essentially the same when played for a listener on any type of music generating platform (headphone, amplifier, speaker, smartphone, computer, and the like). Yet another distinct advantage hereof is the inclusion of an ear fatigue time alert for a subject sound engineer in order to permit temporary discontinuing a mixing session for the benefit of maximizing auditory sensitivity and effects for such a sound engineer to ensure optimal mixing results in relation to the hearing capabilities of such a person at and during a specific mixing session.

Accordingly, this inventive disclosure encompasses an audio mixing and evaluating program for treatment of separately recorded non-bass and bass track components, said program comprising a high-pass filter for utilization with at least one recorded non-bass track, and a two-level bass track filter; wherein said high-pass filter applies both a distortion reduction component combined with maximum ear sensitivity frequency level treatment, and wherein said two-level bass filter separates a low-frequency bass portion and a high-frequency bass portion for separate mixing and ultimate combining with said filtered non-bass track component. The same program may further include an ear fatigue alert component to notify the user when a certain period of time has passed during the utilization of such a program during a sound engineering operation to suggest a rest period for optimal auditory sensation utilizations during an underlying music mixing procedure. The overall disclosure also encompasses such a music mixing procedure comprising the method of: i) providing a high-pass filter for utilization with at least one recorded non-bass track, and a ii) providing a two-level bass track filter, iii) recording at least one non-bass track and at least one bass track, iv) separating said at least one non-bass track from said at least one bass track, v) applying said high-pass filter to said at least one non-bass track, vi) applying said two-level bass track filter to said at least one bass track; and vii) combining the resultant filtered at least one non-bass track and filtered at least one bass track; wherein said high-pass filter applies both a distortion reduction component combined with maximum ear sensitivity frequency level treatment, and wherein said two-level bass filter separates a low-frequency portion and a high-frequency portion. It is well understood that such unintended sound qualities as described herein may or may not include distortions in micrphone and like recorded devices.

The disclosure thus includes a system that utilizes such a non-bass track filter (translation) method, a two-level bass track filter method, an ear fatigue monitoring method (as an add-on that is, in one potentially preferred embodiment, included with the other two components), as well as an alternately included comparison method, to improve upon recorded sound/music issues. With regard to the translation method, there exists speaker translation issues between the audio systems in a sound studio, and various consumer listening systems. The instant disclosure improves the translation with a precise high pass filtering of low frequencies that mislead the ear during the mixing process, so that the highest frequency, and thus highest resolution, parts of a mix can be evaluated with more precision. Additionally, when sound engineers are working to adjust bass levels, bass frequency translation inaccuracies can arise due to imbalanced harmonic and fundamental ranges of recorded bass sources. The instant invention solves this by providing independent adjustment of the harmonic and fundamental ranges of a bass source, primarily bass guitar and bass drums, in context of the high pass, evaluate and impart the adjustment in the most detail.

The ear fatigue monitoring method component provides sound engineers a beneficial alert in situations where they often experience flawed decision making due to ear fatigue, and have no visual reference of when ear fatigue has set in. The disclosed system runs a short term and long term timer, triggered when audio flows through it, to show when ear fatigue may be a factor. It can take SPL into account. It also counts the rest time when the audio playback stops, giving the audio engineer clear indication of when ear fatigue recovery has transpired.

As it thus concerns an alternatively included comparison method component, there exists a problem of inaccurate comparisons while evaluating audio quality due to cognitive biases and differences in loudness. The instant disclosure solves this by balancing loudness and adding a randomized and blind function while evaluating audio that flows through it.

The two- (or perhaps three- and alternatively four-) method component system/program/method provides the following improvements over the state of the art:

1. Speaker translation issues widely persist in sound engineering, and the instant invention's improvement of applying a high pass filter made specifically for focusing on the parts of the mix with the highest frequency and thus resolution, allows an improvement in translation during the audio evaluation process. It minimizes the effects of inaccurate bass reproduction in acoustic environments that are not ideal, helping to avoid acoustical issues negatively impacting the adjustment of a recording.
2. The disclosed system's improvement of adding a high pass filter to the listening while limiting the user to only two filters represents a quick and easy way to improve bass translation.
3. The disclosed system's improvement of creating an automatic real time measurement of audio fatigue allows sound engineers to monitor their ear fatigue, and avoid making critical decisions during it. The convenience of this device and its automatic nature ensure a low impact on the time impact on the user's schedule.
4. The disclosed system's improvement of combining real-time loudness matching together with randomized blind testing in the form of an audio plugin allows for better decisions to be made throughout the sound engineering workflow.

To accomplish these improvements, the individual methods incorporate the following steps and component:

Translation Method. This tool consists of two parts, the first is a high-pass audio filter that is constructed to remove bass while minimizing filter distortion. The second part is a set of two audio filters that can either be implemented as shelves or bells, with center frequencies set so the user can adjust the fundamental and harmonic portions of a bass recording independently. Using this method of the high pass in conjunction with the bass recording filters, allows the user to create recordings with balance between the fundamental and harmonic bass instruments, and hear a mix in a way that translates to other listening systems in an accurate way. As noted above, high-pass filter of this type have been limited to applications connected with microphones during actual recording activities; nothing has been implemented as now disclosed wherein such a high-pass filter is provided with the actual recorded material. Thus, the capabilities uncovered with this disclosure have heretofore not been visited, let alone understood, by the ordinarily skilled artisan in this industry.

Two-Level Bass Mixing Component. The separated bass track (from the translation method component, for instance) is essentially separated into upper and lower frequency divisions for further mixing treatments with bass filter components. This allows for the sound engineer to "massage" the bass track completely for more robust integration between the two separate frequencies as well as to combine with the non-bass track component for, as noted previously, an overall effect that maximizes the capability of the resultant sound qualities for play on any type of sound producer (speaker, headphone, earphone, smartphone, amplifier, computer, etc.) without any appreciable difference. In other words, it is common that recorded music nowadays suffers from sound qualities that result in playback at noticeably different levels. For example, earphones may provide limited treble with higher bass levels inherently, while computers provide muffled sound results, car speakers require high levels of adjustments internally to compensate for too-high bass levels in comparison with treble components, stereo amplifiers may further generate low bass with overcompensations for treble outputs, all with the same exact recording (such as from a CD, radio broadcast, downloaded computer file, etc.). The ability to thoroughly mix two separate bass levels to adjust, prior to public dissemination of such a recorded musical piece, and then mix with the translated non-bass track component with maximum ear sensitivity ear levels and reduction of unintended sound quality (and/or low distortion results), provides the music industry a resultant audio file (or other recorded medium) that provides the most uniform audio results so that such varied sound production devices (again, amplifier, computer, smartphone, earphone, headphone, etc.) generate uniform results when played. The two-level bass filter is thus heretofore unknown within the recording industry and provides this unheard of result.

Ear Fatigue Monitoring Method. The invention has a short term ear fatigue timer set to approximately 6 minutes that counts down when audio flows through it. There is a long term ear fatigue timer, which counts down from 12 minutes when audio flows through it. When audio playback stops, it automatically detects it and starts a 2 minute timer ear fatigue reset countdown, that when it expires, indicates to the user that they have rested their ears fully and are free from the effects of ear fatigue. If the ear fatigue reset countdown is interrupted by audio being played back, it resets and the user would have to again stop playback starting at 2 minutes to perform a full rest.

Alternative Comparison Method. The comparison feature has a switch that allows the user to select between two different audio recordings. It has a blind mode so the switching can be performed without visual feedback as to the recording being played. There is a randomize function to randomize the switch position so the user does not know which source is being heard. There is also a loudness matching that occurs continuously between the two input signals that is accomplished by applying a weighted filtering and adjusting the input gain of the signal depending on the input at regular intervals. There is an indicator light that shows the user if both signals are ready to compare.

It should be understand, as well, that the non-bass track filtering operation described herein may be undertaken after any recording has been generated. Thus, even if a single track with, for instance, a singer's voice (or even a guitar line, or keyboard, etc.), is generated, the non-bass track filtering step may be employed to determine both the maximum ear sensitivity level of the track at issue as well as providing reductions (if not complete removal) of sound distortions therein, as well. Such a bass track may also be provided as a single (or multiple) track(s) for filtering purposes within the two-level step, as well, if desired. Thus, the overall system may employ such individual recordings with the filtering steps utilized in relation thereto, then combining each filtered result together for a finished product and still be within the scope of the disclosure and overall invention.

DETAILED DESCRIPTION OF THE DISCLOSED SYSTEM AND DRAWINGS

When judging sound quality, subjective and objective factors are at play according to at least one source. Generally, audio has objective and subjective perceptions and in this source we explore the objective side. This disclosure goes into detail about what objective factors exist, decomposes them, covering how they are measurable and how to advance them. PEMO-Q is one of the more popular methods for this evaluation, while others exist and are in development.

When examining the experience of Geoff Emerick, Bruce Swedien and Bob Clearmountain, listening without bass is a connection linking their experiences. Each of these key engineers describe distinct listening techniques, and express them to be central to their work and accomplishments. The first of the techniques pre-dates the work of Geoff Emerick, as he attributes the technique to Norman Smith, an earlier engineer for The Beatles also known for working with the highly regarded band, Pink Floyd. We can't be certain how the technique originated, but we do know that it played a role in the success of one of the most popular musical groups of all-time which was noted for recordings that had a unique sound.

Today, listening systems with an extended bass range are common and relatively inexpensive in audio engineering. Bass levels of a mix can be set with precision using these systems, however, mixing with them in full-range mode may detract from the potential mix quality and the ability of a mix to translate well to a variety of systems. In the past, full range systems were less common. Also, there was a distinct elimination of the bass frequencies that helped focus in on the frequencies to which we are most sensitive with the techniques employed by Smith, Emerick, Swedien and Clearmountain. Also, with the distinct techniques used by each of these engineers, we may find that different options for evaluation could yield unique styling to the material at hand.

Figure 3:
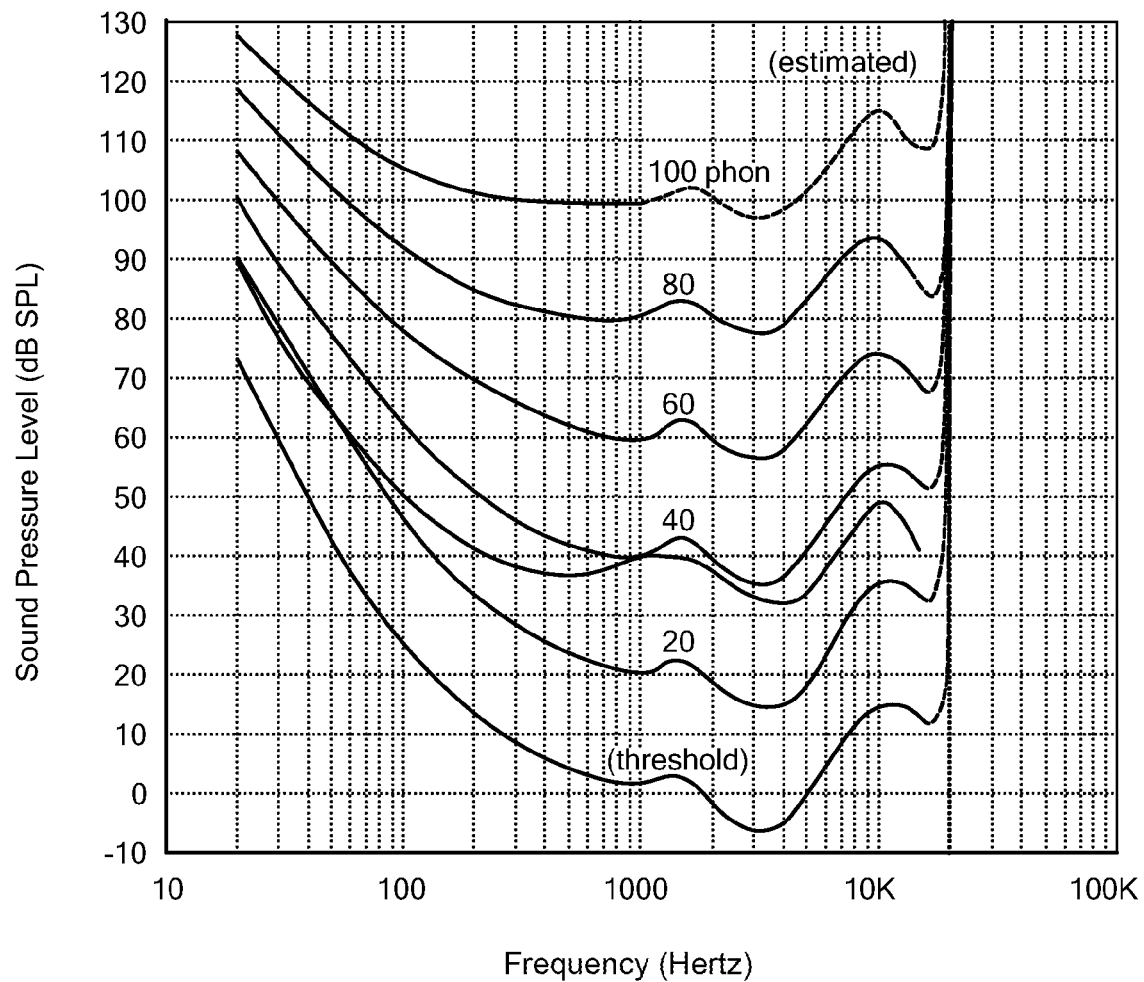
FIG. 3 is a prior art graphical representation of an ISO 226:2003 Curve set at different frequencies.

The sensitivity of the human ear and the nature of the bass frequency range are significant factors when considering the use of a high pass filter for evaluation. While the Fletcher-Munson curves may be the most widely-known description of the sensitivity of the ear, they were later followed by the Robinson-Dadson curves and most recently by (ISO 226: 2003) (FIG. 3 Prior Art). A general understanding from this research is that the ear is most sensitive around 3 kHz with a peaks there and diminished results above and below. Humans have little sensitivity to bass frequencies, as well as frequencies as they approach the Nyquist limit. It is also a matter of comfort, for example, if a pure 50 Hz tone were played in a room, it would be far more comfortable to the ear than a tone at 3 kHz, or even 10 kHz at the same loudness level.

Using a high pass filter to evaluate audio causes a distortion that would not be concluded from other sources. When high pass filtering is applied, it affects frequency ranges significantly above the cutoff frequency. We also understand from this source that speakers can act as high pass filters, just as an analog or digital filter could. When considering this understanding, together with the techniques employed by Smith, Emerick, Swedien and Clearmountain, it is apparent that the classic evaluation techniques accounted for subtle distortions caused by filtering, while simultaneously focusing the audio engineer on the frequencies which are most sensitive to the human ear.

Bass frequencies wavelengths are longer and thus less character is possible in the bass range. While no source imported into this research that makes this claim, it is common knowledge to virtually all audio engineers with a basic understanding of the nature of the audible frequency range. Frequencies are measured in Hertz (Hz), a measure per unit of time in seconds. The human range of hearing spans from 20 Hz to 20,000 Hz. Because of this wide range, Hertz relating to sound is typically represented on a logarithmic scale, as a linear scale would be too wide and would not practically depict audible frequency energy. Because of the nature of the depictions and the nature of the frequency sensitivity of the ear, we understand that exponentially more energy is contained in the lower frequencies. It logically follows that exponentially less character is possible in the lower frequencies than in those higher. From this it is easy to see that bass frequencies do not carry much character. With bass, the greatest factor is loudness and transient characteristics. Combining this with the notion that the ear is less sensitive to bass frequencies, we see that this range is unique from those upper ranges to which we are less sensitive but that can carry exponentially higher character.

Thus, it has been understood herein within this disclosure that bass frequencies obscure one's decision making during mixing. They are more pleasing to the ear, use far more energy, have exponentially less resolution than the ranges above, and are reproduced with the highest variability among different listening systems. From this, it has been determined that to craft a mix with higher translation and with a focus on the frequencies that contain character, we may mix without the bass frequencies present. This is tantamount to using a zoom feature when working in the visual modality. From there it was then realized that there are discrete ways to best implement a bass filter to yield discrete stylistic results for the user.

An optimal high-pass filter for listening evaluation has thus been crafted herein. Such a high-pass filter is used to eliminate bass frequencies, thus the name high-pass, as higher frequencies are allowed to pass, while lower frequencies are not.

All pass filters have a cutoff frequency and a slope. All professional audio engineers are familiar with these parameters. However, there are other details that can affect the filter performance.

There are several filter types, including the Bessel type, which apparently has the widest, most gradual crossover region with a gentle dip when summed in usage as a crossover. There are other filter types that have their own benefits, which should be considered when selecting the optimal high pass filter for filtering these frequencies. It is likely that a Bessel filter would be the most useful for the purpose of evaluating audio.

High-pass filters have an attribute called the filter order. A higher filter order will allow for increased accuracy. Particularly a $4^{th}$ or $6^{th}$ order filter would provide the highest possibly audible quality. However, when using a higher filter order, the slope will be affected and it may be very best to find the slope and order combination that best fits to the curve shown in (ISO 226:2003).

The inventive high pass filter design and utilization disclosed herein for evaluating audio centers around the sensitivity of the human ear (or possibly, if desired, around other listening needs). Using the sensitivity of the ear allows the user to focus on those frequencies to which we are most sensitive. However, this does still include de-emphasized bass frequencies that may not be reproduced by smaller listening systems. With this in mind, slopes that cut more bass provide the highest zooming effect and produce the highest translatability.

Thus, one separate non-bass tracks from bass tracks (such as those that are well understood by the ordinarily skilled artisan). Once separated, the non-bass track component(s) is then, in its recorded state, filtered by the same or a different type of filter (Bessel and the like) in order for the sound engineer to maximum ear sensitivity measurements at 3 Hz (and the like); the filter likewise acts, on the recorded track component(s) to remove distortions therefrom (see FIGS. 4-10, for instance, as the resultant curves are smooth without any appreciable or noticeable distortion levels). The resultant filtered non-bass track component(s) is then retained for combination and mixing with the bass track. To that end, the bass track is then filtered again to separate the high frequency portion from the low frequency portion, allowing for "zooming" in on each individual track portion for more effective treatment. Such a filter step allows for the sound engineer the ability to work his or her magic, as it were, and effectively blend the two separate track portions together. In the past, as noted above, such a bass track would only be treated as a single component, without any means to rework and/or mix such a heavy frequency recorded component beyond the single separation from the non-bass track. Thus, with the ability to further refine the bass track portions in this manner, the sound engineer has a greater palette for coloring the resultant musical product and integrate the same to a more robust level with the non-bass track. The resultant effect is that the finished product is provided with a uniformity in sound quality such that any sound producing device will ostensibly provide the same basic listening results for the user (dependent more on individual auditory qualities, rather than the sound producing device itself). Such has heretofore been unattained since the bass lines of standard recorded music has been treated as a single track or component and the non-bass track has either exhibited high levels of distortions or is targeted to maximum ear sensitivity levels, not both.

Additionally, as noted above, the overall mixing program accords the sound engineering an alert component that indicates when a certain amount of time has passed during high intensity (for instance) audio exposure during such a mixing operation. The ability to limit such continuous exposure helps the sound engineer to maximize his or her capabilities without suffering ear fatigue.

Evaluation of audio also includes comparison, and the remaining discussion is in regard to this topic. FIGS. 4-10 provide different evaluation curves for the sound engineer to determine if the filtered tracks have been undertaken to the desired levels. Comparison may include comparing one recording to another, or one processed version of a recording to another processed version.

Because differences in loudness of approximately 0.41 dbSPL are detectable by the ear per the popular research, all difference thresholds for comparison should be lower than this level. This can be made even more exact by implementing the loudness curves in (ISO 226:2003), so that all thresholds use this filtering to ensure that differences are according to the sensitivity of the ear.

These disclosed comparison devices thus involve an evolution beyond the earlier ideas of sound recording improvements noted above.

Of the current comparison methods, ABX testing is perhaps the most noted. While ABX testing is practical for research and controlled experiments, it would not be very practical in the course of an audio engineer's daily work and evaluation. In these prior situations, even more stringent statistical controls and evaluations are in place (or at least suggested) than in the standard ABX fare; however, these advancements, including double blind testing is generally not practical for audio engineering purposes and for speed of evaluation. Usage of a third random element may not be practical for some audio engineering tasks but may be for others, so the inclusion of this idea is something that can be considered in the crafting of a comparison device.

Recently, cross-modal interplay has been considered, which is interplay between vision and audition. In consideration of this research, an advanced comparison device would include a feature that would blank or otherwise diminish the visual modality during audition. In this way, the device interface would not affect audition, while minimizing any sacrifice in the graphical appeal of the comparison device.

Proposed then have been three divisions for evaluation including stimulus response, pleasantness of sound, and identifiability of sounds or sound sources. For audio engineers, the mode of evaluation may instead be along the lines of frequency range evaluation, and then temporal evaluation where the listening focuses primarily on timing and dynamics. This thinking may be combined now with prior considerations which describe that there are both objective and subjective modes of listening, with the objective modes being possible upon which to construct meters. To that end, prior work suggests that PEMO-Q is one of the most popular evaluation methods, while there will be others that follow. The best comparison tools will help to prompt users to evaluate audio in different ways. Also, as an evolution of the intellectual property claims involving voting, a rating scale may be more useful to gauge how program material at hand measure within prompted categories of evaluation.

Figure 1:
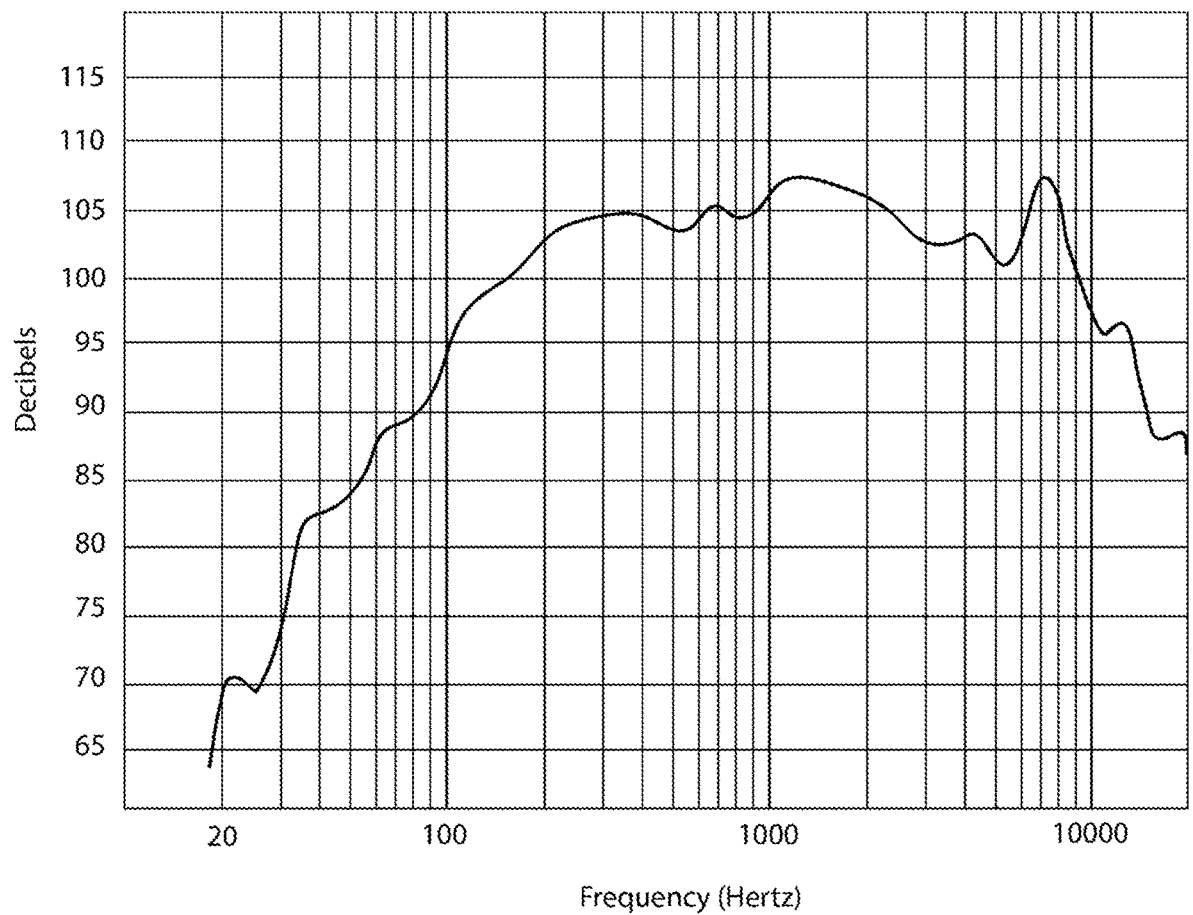
FIG. 1 is a prior art graphical representation of a typical Auratone Frequency Response.
Figure 2:
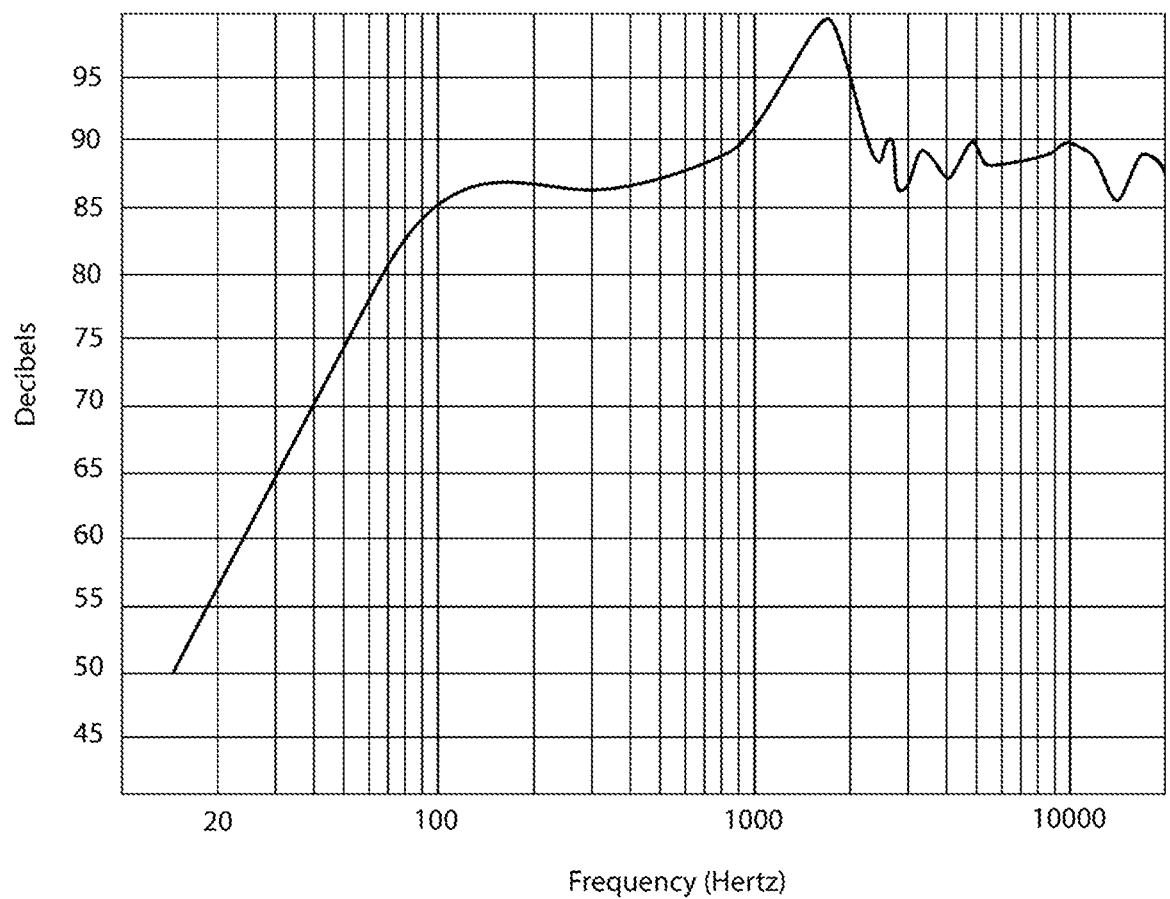
FIG. 2 is a prior art graphical representation of a typical Yamaha NS10 Frequency response.
Figure 4:
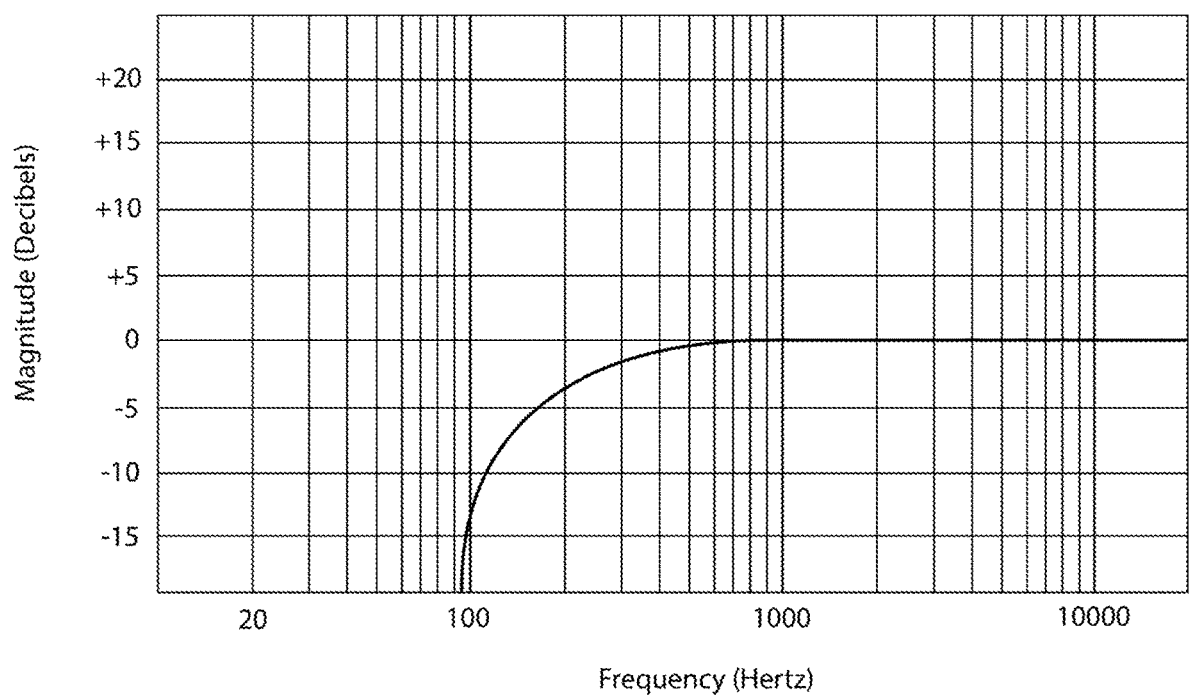
FIG. 4 is an inventive Primary Non-Bass Track Filter curve graphical representation.
Figure 5:
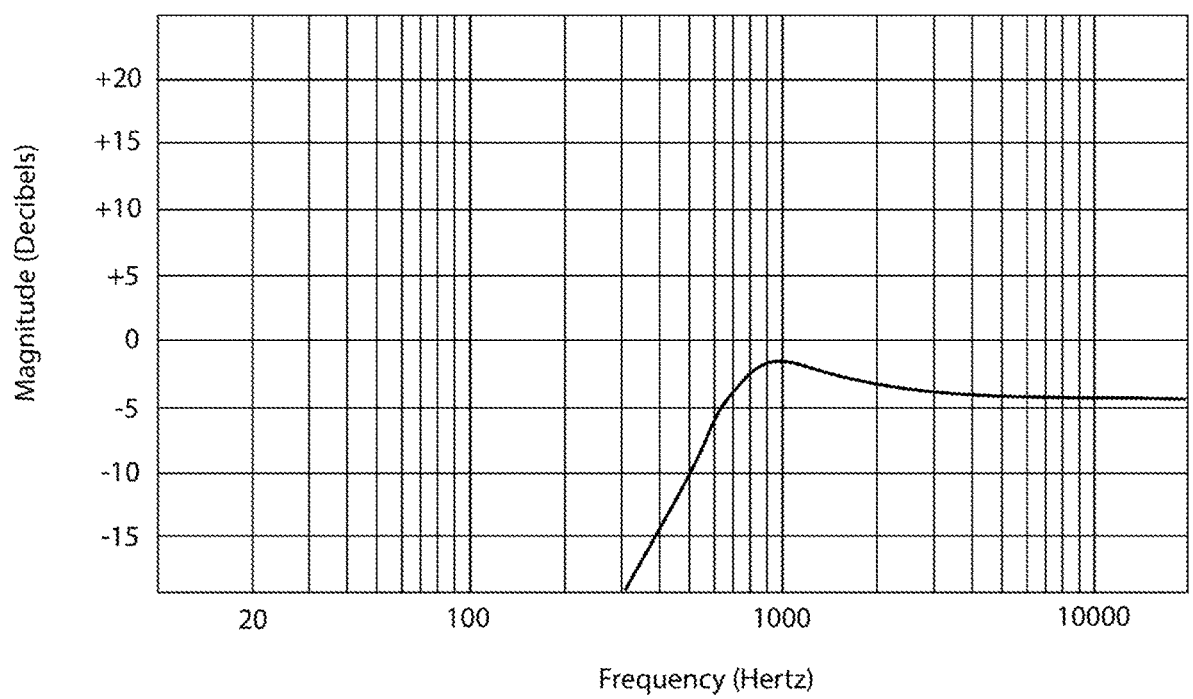
FIG. 5 is a graphical representation of a curve for a device evaluation result after filtering.
Figure 6:
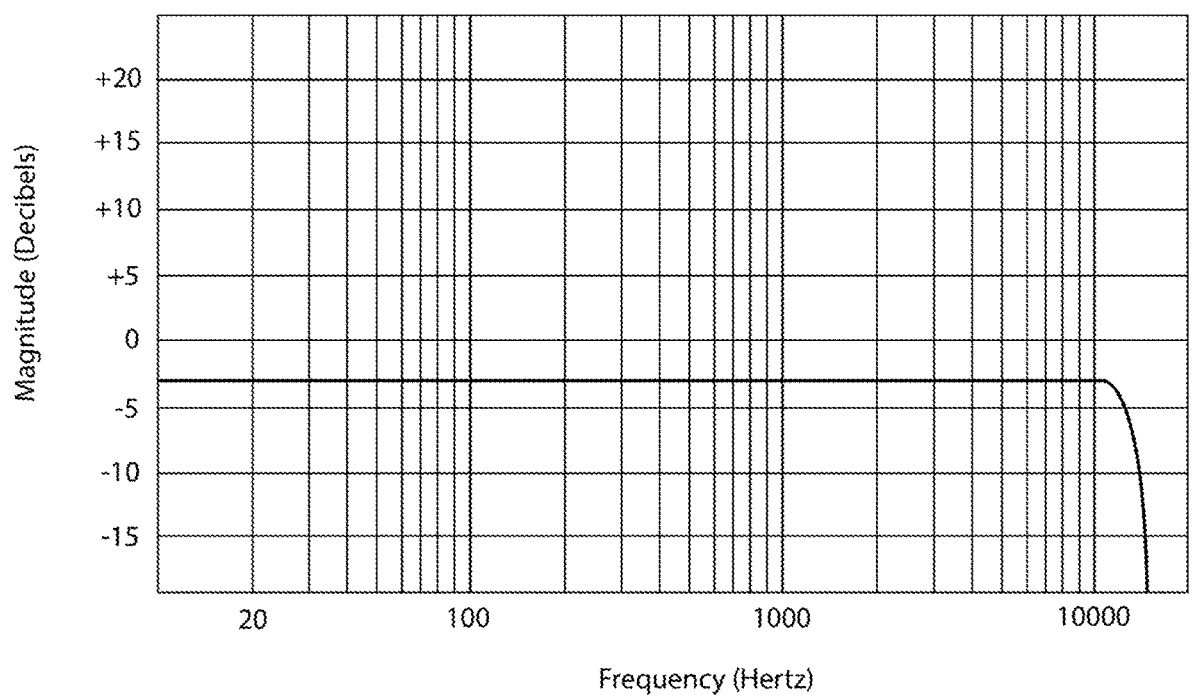
FIG. 6 is a graphical representation of a curve showing FM radio typical results for a filtered non-bass track.
Figure 7:
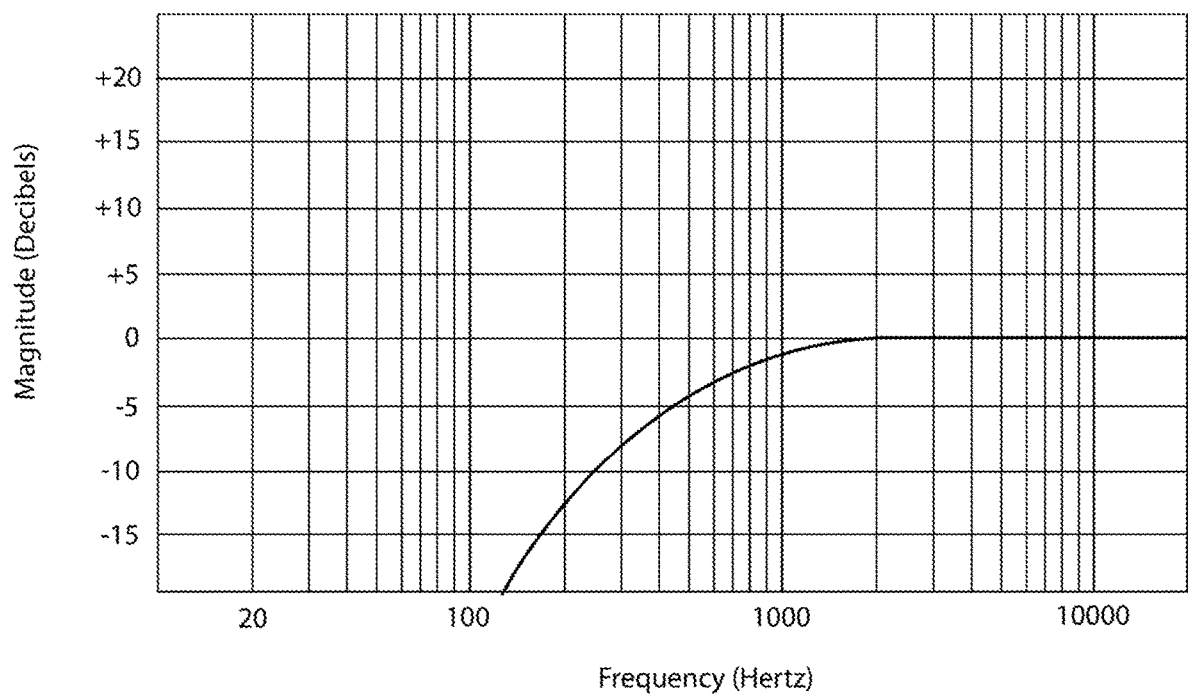
FIG. 7 is a graphical representation of a curve showing a Mastering Harshness evaluation of a filtered non-bass track.
Figure 8:
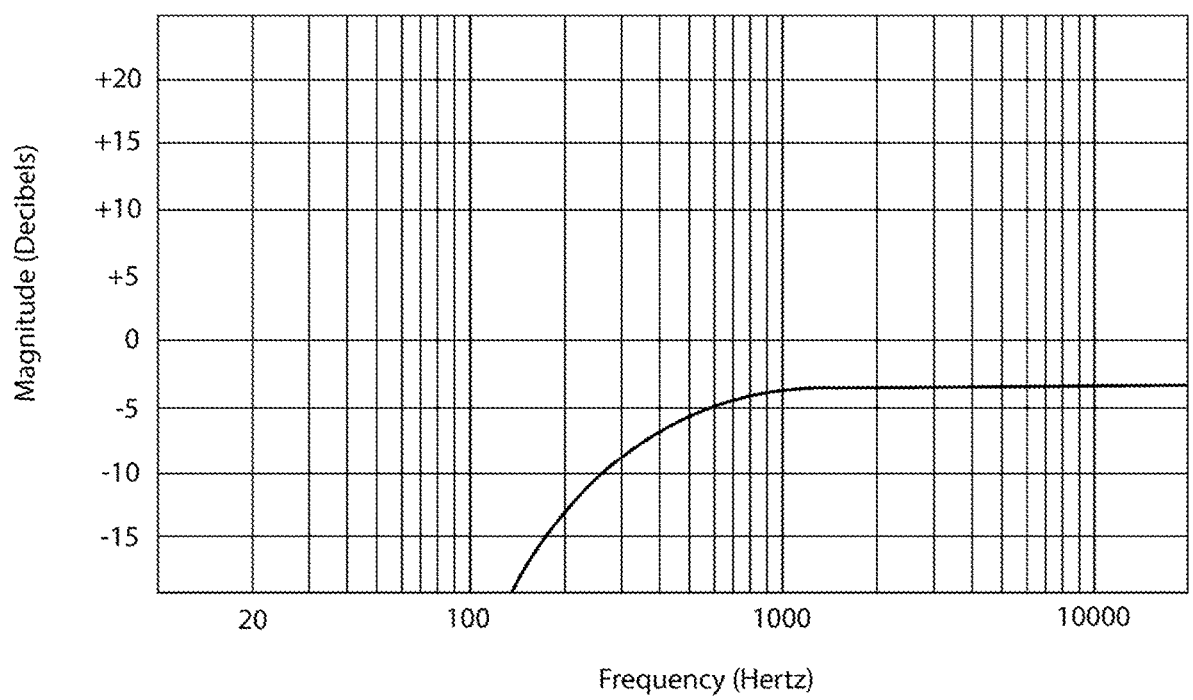
FIG. 8 is a passive evaluation graphical representation of a curve showing a filtered non-bass track.
Figure 9:
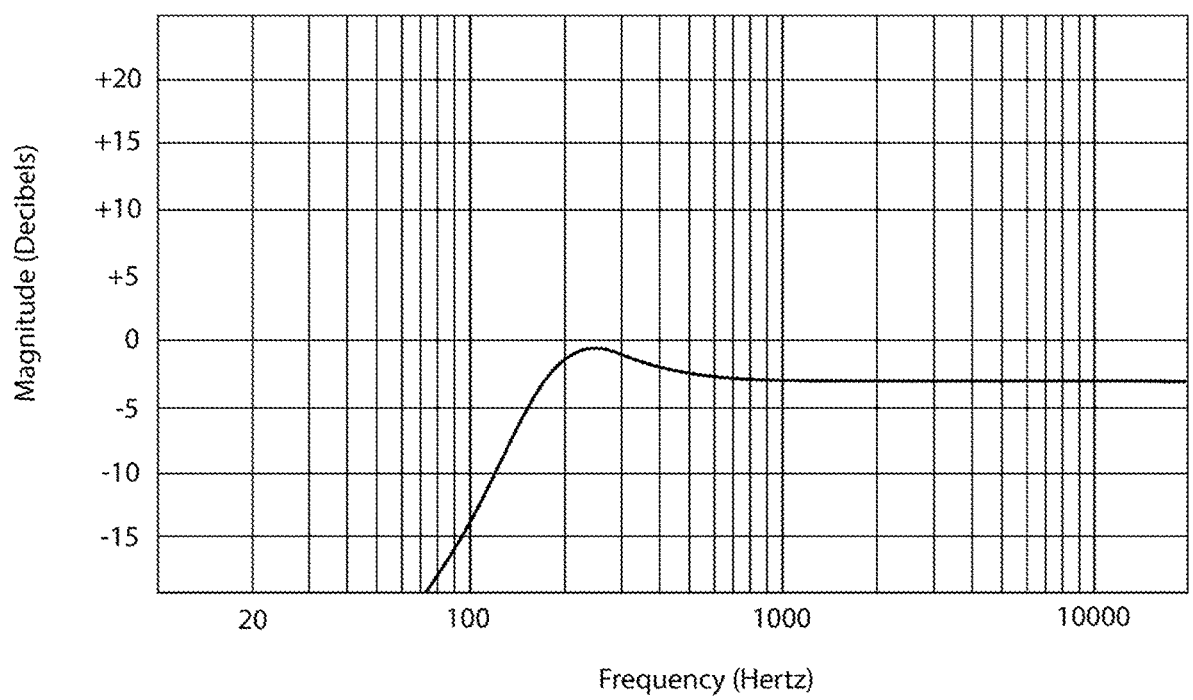
FIG. 9 is a graphical representation of a curve showing total quality review for a filtered non-bass track.
Figure 10:
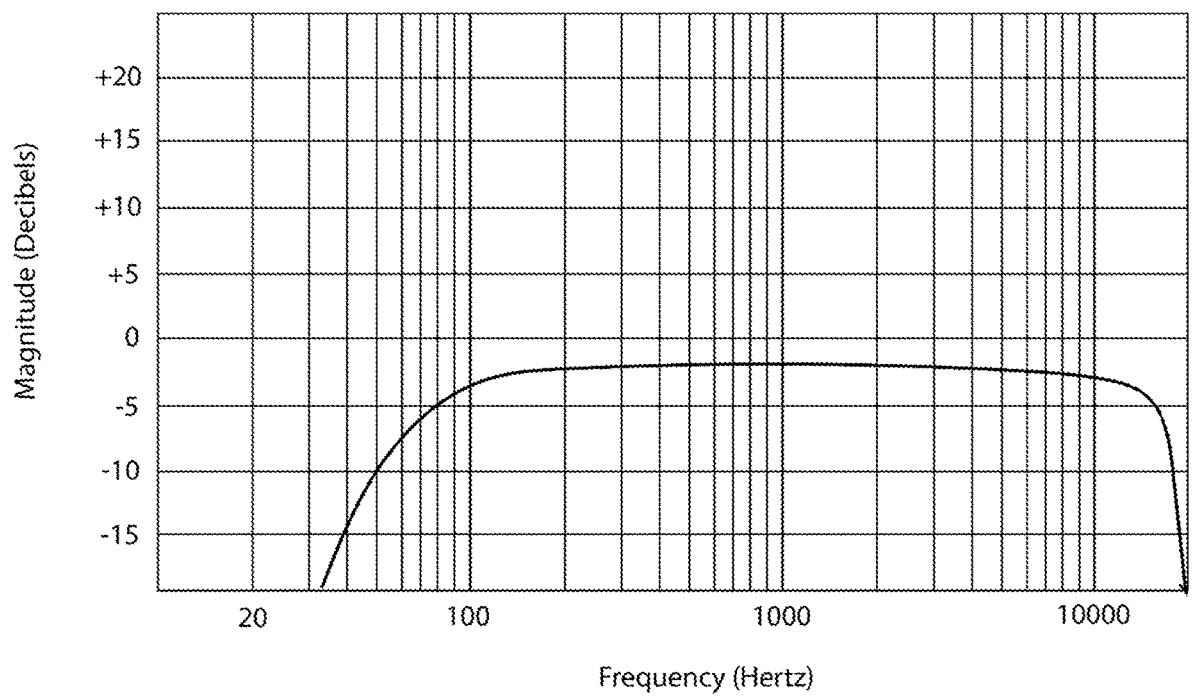
FIG. 10 is a graphical representation of a curve showing Auratones-like curve without nonlinearity for a filtered non-bass track.

This two-component (possibly three- and/or four-component) system thus overcomes such prior limitations with highly effective results. FIGS. 4 through 10 provide graphical representations of the overall effectiveness of such multi-track treatments, particularly in terms of the smooth (low unintended sound qualities and/or distortion) results (as compared with, for instance, those in Prior Art FIGS. 1 and 2). The maximum ear sensitivity levels are obtained through the high-pass filter application to the recorded non-bass track component(s) as shown in FIG. 4, as well, a result heretofore unattained within the recording industry, precisely because of the lack of utilizing anything that can capture such low distortion and maximum ear sensitivity results. Combined with the results generated as to high frequency and low frequency separated bass track recordings and applying the resultant treatments (mixing to optimum levels separately, in view of the integration with the non-bass track results) again provide effects that have heretofore been unexplored (and hence unattained) within the recording industry.

While the technique of listening without bass dates back to the earliest popular recordings, the technique itself may not have been duly acknowledged. Herein disclosed are the best ways of constructing a listening tool that would help in evaluating bass, particularly in terms of two-level separated mixing methods.

Sound engineering is an area where the utmost quality is demanded. This research, and the tools that can be constructed according to it, will help increase the quality of work for virtually any engineer who is not currently employing similar techniques, and will help increase the quality of those who are accomplishing these tasks in a more manual or less accurate way.

Although specific embodiments of the invention have been disclosed, those having ordinary skill in the art will understand that changes can be made to the specific embodiments without departing from the spirit and scope of the invention. The scope of the invention is not to be restricted, therefore, to the specific embodiments, and it is intended that the description herein cover any and all such applications, modifications, and embodiments within the scope of the present invention.

What is claimed is:

1. An audio mixing and evaluating method for generating a single mixed audio recording in a sound recording studio including the treatment of separately recorded non-bass and bass track components, said method comprising:

i) separately recording of at least one non-bass track and at least one bass track component of a musical audio recording;

ii) providing a high-pass filter for utilization with said at least one recorded non-bass track, wherein said high-pass filter includes a) a distortion reduction component and b) a maximum ear sensitivity frequency level treatment component to indicate the passage of a certain period of time during the utilization of said method to suggest a rest period for optimal auditory sensation utilizations;

iii) providing a two-level bass track filter for utilization with said at least one recorded bass track, wherein said bass track filter separates low-frequency and high-frequency bass track portions;

iv) applying said high-pass filter of step "ii" to said at least one recorded non-bass track to generate at least one filtered non-bass track component exhibiting distortion reduction results and maximum ear sensitivity frequency level treatment results;

v) applying said two-level bass track filter of step "iii" to said at least one recorded bass track to generate at least one filtered bass track component exhibiting separated low-frequency and high-frequency resultant bass track portions; and vi) combining said at least one filtered non-bass track component of step "iv" with said at least one filtered bass track component of step "v" to generate said resultant mixed audio recording.

* * * * *